United States Patent [19]

Tso et al.

[11] Patent Number: 5,004,692
[45] Date of Patent: Apr. 2, 1991

[54] CLONING AND EXPRESSION OF PHOSOPHOLIPASE C GENES

[75] Inventors: J. Yun Tso, Menlo Park; Cary L. Queen, Palo Alto, both of Calif.

[73] Assignee: Protein Design Labs, Inc., Mountain View, Calif.

[21] Appl. No.: 132,387

[22] Filed: Dec. 15, 1987

[51] Int. Cl.$^5$ .......................... C12N 9/00; C12N 9/14
[52] U.S. Cl. .................................... 435/183; 435/195; 435/240.1; 435/252.3; 435/252.33; 435/320.1; 536/27
[58] Field of Search ............... 435/320, 68, 70, 172.3, 435/183, 195, 240.1, 849; 536/27

[56] References Cited

U.S. PATENT DOCUMENTS

| | | | |
|---|---|---|---|
| 4,140,579 | 2/1979 | Moncla | 195/99 |
| 4,140,754 | 2/1979 | Iwasa | 424/12 |

OTHER PUBLICATIONS

Microgenie ® User Manual, Beckman Instruments, Dec. 1988.
Pritchard, A. E. and Vasil, M. L., 1986, J. Bact., 167:291-298.
Krug, E. and Kent, C., 1984, Arch. Biochem. Biophys., 231(20:400-410).
Yamakawa, Y. and Ohsaka, A., 1977, J. Biochem., 81:115-126.
Kikutani, H. et al., 1986, Cell, 47:657-665, Dec. 5, 1986.

*Primary Examiner*—Richard A. Schwartz
*Attorney, Agent, or Firm*—Townsend and Townsend

[57] ABSTRACT

Improved means for producing Clostridium Phospholipase C (PL) polypeptides based on the cloning and expression of recombinant DNA segments containing Clostridium PLC genes and fragments. The DNA segments are operably linked to host specific expression control sequences for exogenous production of Clostridium PLC, or fragments thereof, substantially free from naturally-associated Clostridium gene products.

18 Claims, 4 Drawing Sheets

```
                                    30                                              60
ATG AAA AGA AAG ATT TGT AAG GCG CTT ATT TGT GCC GCG GTA GCA ACT ACG CTA TGG GCT
Met Lys Arg Lys Ile Cys Lys Ala Leu Ile Cys Ala Ala Leu Ala Thr Thr Leu Trp Ala
                                    90                                             120
GGG GCA TCA ACT AAA GTC TAC GCT TGG GAT GGA AAG ATT GAT GGA ACA GGA ACT CAT GCT
Gly Ala Ser Thr Lys Val Tyr Ala Trp Asp Gly Lys Ile Asp Gly Thr Gly Thr His Ala
                                   150                                             180
ATG ATT GTA ACT CAA GGG GTT TCA ATC TTA GAA AAT GAT CTG TCC AAA AAT GAA CCA GAA
Met Ile Val Thr Gln Gly Val Ser Ile Leu Glu Asn Asp Leu Ser Lys Asn Glu Pro Glu
                                   210                                             240
AGT GTA AGA AAA AAC TTA GAG ATT TTA AAA GAG AAC ATG CAT GAG CTT CAA TTA GGT TCT
Ser Val Arg Lys Asn Leu Glu Ile Leu Lys Glu Asn Met His Glu Leu Gln Leu Gly Ser
                                   270                                             300
ACT TAT CCA GAT TAT GAT AAG AAT GCA TAT GAT CTA TAT CAA GAT CAT TTC TGG GAT CCT
Thr Tyr Pro Asp Tyr Asp Lys Asn Ala Tyr Asp Leu Tyr Gln Asp His Phe Trp Asp Pro
                                   330                                             360
GAT ACA GAT AAT AAT TTC TCA AAG GAT AAT AGT TGG TAT TTA GCT TAT TCT ATA CCT GAC
Asp Thr Asp Asn Asn Phe Ser Lys Asp Asn Ser Trp Tyr Leu Ala Tyr Ser Ile Pro Asp
                                   390                                             420
ACA GGG GAA TCA CAA ATA AGA AAA TTT TCA GCA TTA GCT AGA TAT GAA TGG CAA AGA GGA
Thr Gly Glu Ser Gln Ile Arg Lys Phe Ser Ala Leu Ala Arg Tyr Glu Trp Gln Arg Gly
                                   450                                             480
AAC TAT AAA CAA GCT ACA TTC TAT CTT GGA GAG GCT ATG CAC TAT TTT GGA GAT ATA GAT
Asn Tyr Lys Gln Ala Thr Phe Tyr Leu Gly Glu Ala Met His Tyr Phe Gly Asp Ile Asp
                                   510                                             540
ACT CCA TAT CAT CCT GCT AAT GTT ACT GCC GTT GAT AGC GCA GGA CAT GTT AAG TTT GAG
Thr Pro Tyr His Pro Ala Asn Val Thr Ala Val Asp Ser Ala Gly His Val Lys Phe Glu
                                   570                                             600
ACT TTT GCA GAG GAA AGA AAA GAA CAG TAT AAA ATA AAC ACA GCA GGT TGC AAA ACT AAT
Thr Phe Ala Glu Glu Arg Lys Glu Gln Tyr Lys Ile Asn Thr Ala Gly Cys Lys Thr Asn
                                   630                                             660
GAG GCT TTT TAT ACT GAT ATC TTA AAA AAC AAA GAT TTT AAT GCA TGG TCA AAA GAA TAT
Glu Ala Phe Tyr Thr Asp Ile Leu Lys Asn Lys Asp Phe Asn Ala Trp Ser Lys Glu Tyr
                                   690                                             720
GCA AGA GGT TTT GCT AAA ACA GGA AAA TCA ATA TAC TAT AGT CAT GCT AGC ATG AGT CAT
Ala Arg Gly Phe Ala Lys Thr Gly Lys Ser Ile Tyr Tyr Ser His Ala Ser Met Ser His
                                   750                                             780
AGT TGG GAT GAT TGG GAT TAT GCA GCA AAG GTA ACT TTA GCT AAC TCT CAA AAA GGA ACA
Ser Trp Asp Asp Trp Asp Tyr Ala Ala Lys Val Thr Leu Ala Asn Ser Gln Lys Gly Thr
                                   810                                             840
GCG GGA TAT ATT TAT AGA TTC TTA CAC GAT GTA TCA GAG GGT AAT GAT CCA TCA GTT GGA
Ala Gly Tyr Ile Tyr Arg Phe Leu His Asp Val Ser Glu Gly Asn Asp Pro Ser Val Gly
                                   870                                             900
AAG AAT GTA AAA GAA CTA GTA GCT TAC ATA TCA ACT AGT GGT GAG AAA GAT GCT GGA ACA
Lys Asn Val Lys Glu Leu Val Ala Tyr Ile Ser Thr Ser Gly Glu Lys Asp Ala Gly Thr
```

FIG._I.

PAGE I OF 2

```
                                          930                                                        960
GAT GAC TAC ATG TAT TTT GGA ATC AAA ACA AAG GAT GGA AAA ACT CAA GAA TGG GAA ATG
Asp Asp Tyr Met Tyr Phe Gly Ile Lys Thr Lys Asp Gly Lys Thr Gln Glu Trp Glu Met
                                      990                                                          1020
GAC AAC CCA GGA AAT GAT TTT ATG ACT GGA AGT AAA GAC ACT TAT ACT TTC AAA TTA AAA
Asp Asn Pro Gly Asn Asp Phe Met Thr Gly Ser Lys Asp Thr Tyr Thr Phe Lys Leu Lys
                                     1050                                                          1080
GAT GAA AAT CTA AAA ATT GAT GAT ATA CAA AAT ATG TGG ATT AGA AAA AGA AAA TAT ACA
Asp Glu Asn Leu Lys Ile Asp Asp Ile Gln Asn Met Trp Ile Arg Lys Arg Lys Tyr Thr
                                    1110                                                           1140
GCA TTC TCA GAT GCT TAT AAG CCA GAA AAC ATA AAG ATA ATA GCA AAT GGA AAA GTT GTA
Ala Phe Ser Asp Ala Tyr Lys Pro Glu Asn Ile Lys Ile Ile Ala Asn Gly Lys Val Val
                              1170
GTG GAC AAA GAT ATA AAC GAG TGG ATT TCA GGA AAT TCA ACT TAT AAT ATA AAA TAA
Val Asp Lys Asp Ile Asn Glu Trp Ile Ser Gly Asn Ser Thr Tyr Asn Ile Lys End
```

FIG_1.
PAGE 2 OF 2

```
      30                                          60
ATG AAA GCT TTA AAA AAA GTA TCT AAT ATA CTG TGC GTA TTA GGT TTA TGT ACT CTT ATG
Met Lys Ala Leu Lys Lys Val Ser Asn Ile Leu Cys Val Leu Gly Leu Cys Thr Leu Met
                           90                                          120
GGG GGT ACT TCT TAT GCA TGG GAT GGT AAA AAA GAT GGA ACA GGG ACA CAT TCA TTA ATA
Gly Gly Thr Ser Tyr Ala Trp Asp Gly Lys Lys Asp Gly Thr Gly Thr His Ser Leu Ile
                           150                                         180
GCA GAA CAT GGG TTA AGT ATG CTA AAC AAT GAT TTA AGT GGA AAT GAA TCT CAG CAA GTT
Ala Glu His Gly Leu Ser Met Leu Asn Asn Asp Leu Ser Gly Asn Glu Ser Gln Gln Val
                           210                                         240
AAG GAT AAT ATT AAA ATT TTA AAT GAA TAC TTA GGG GAT TTA AAG TTA GGG TCT ACA TAT
Lys Asp Asn Ile Lys Ile Leu Asn Glu Tyr Leu Gly Asp Leu Lys Leu Gly Ser Thr Tyr
                           270                                         300
CCA GAT TAC GAT CCT AAC GCA TAT GAT CTA TAT CAA GAT CAT TTC TAT GAT CCT GAC ACT
Pro Asp Tyr Asp Pro Asn Ala Tyr Asp Leu Tyr Gln Asp His Phe Tyr Asp Pro Asp Thr
                           330                                         360
GGA AAC AAT TTT ACT ATT GAT AAT AGT TGG TAT GCA TCA TAT CCT ATA TAT GAT ACA AGC
Gly Asn Asn Phe Thr Ile Asp Asn Ser Trp Tyr Ala Ser Tyr Pro Ile Tyr Asp Thr Ser
                           390                                         420
AGA AAC TCA GTA AGA AAG TTT GCT ACA TTA GCT AAA AAT GAA TGG GAA AAG GGA AAT TTT
Arg Asn Ser Val Arg Lys Phe Ala Thr Leu Ala Lys Asn Glu Trp Glu Lys Gly Asn Phe
                           450                                         480
AAA GAA GCT ACA TTC CTT TTA GGC CAA GGA TTA CAT TAT CTA GGG GAT TTA AAT ACT CCA
Lys Glu Ala Thr Phe Leu Leu Gly Gln Gly Leu His Tyr Leu Gly Asp Leu Asn Thr Pro
                           510                                         540
TAT CAT GCT TCA AAT GTA ACT GCA GTG GAT AGT CCT GGA CAT GTT AAA TAT GAA ACT TTT
Tyr His Ala Ser Asn Val Thr Ala Val Asp Ser Pro Gly His Val Lys Tyr Glu Thr Phe
                           570                                         600
GTA GAA GAA AGA AAA GAT AAC TAT GCT TTA AAT ACT TCA GGA AAT GAT ACT ACA TCA GGA
Val Glu Glu Arg Lys Asp Asn Tyr Ala Leu Asn Thr Ser Gly Asn Asp Thr Thr Ser Gly
                           630                                         660
GTA TAT AAA GAA GCT ATG GAA AAT CCA AGT TTT AAT AAA TGG ATG ACA CAA AAC TCT ATA
Val Tyr Lys Glu Ala Met Glu Asn Pro Ser Phe Asn Lys Trp Met Thr Gln Asn Ser Ile
                           690                                         720
AAA TAT GCT AAG ATA GCT AAA GAT TTA TAT TAT AGT CAT TCA ACT ATG AGT CAT AGT TGG
Lys Tyr Ala Lys Ile Ala Lys Asp Leu Tyr Tyr Ser His Ser Thr Met Ser His Ser Trp
                           750                                         780
GAT GAT TGG GAT TAT TCT GGA AGA GAA GCT ATA AAA AAT TCT CAA GTA TGT ACT GCT GGA
Asp Asp Trp Asp Tyr Ser Gly Arg Glu Ala Ile Lys Asn Ser Gln Val Cys Thr Ala Gly
                           810                                         840
TTT TTA TAT AGA TTC ATG AAT GAA GTT TCT AAT GGA AAT ACA GGA GAT AAT GAT TCA TTA
Phe Leu Tyr Arg Phe Met Asn Glu Val Ser Asn Gly Asn Thr Gly Asp Asn Asp Ser Leu
                           870                                         900
ACT AAT GAA TTC AAT ATA GTA TTA AAG ACT GCA GAC AAT AAA TAT GCA GGA ACT GAT GAT
Thr Asn Glu Phe Asn Ile Val Leu Lys Thr Ala Asp Asn Lys Tyr Ala Gly Thr Asp Asp
```

FIG._2.

PAGE 1 OF 2

```
                                        930                                                           960
AAT GTA TAT TTC GGA TTT GAA ACA AAT GAA GGT AAG AAA TTT GAA TGG AAA TTA GAT AAT
Asn Val Tyr Phe Gly Phe Glu Thr Asn Glu Gly Lys Lys Phe Glu Trp Lys Leu Asp Asn
                                        990                                                          1020
GCA GGA AAT GAC TTT GAA AGA AAT CAA GTA GAT AAC TAT ATA TTA AAA ACA AAA GAT GGA
Ala Gly Asn Asp Phe Glu Arg Asn Gln Val Asp Asn Tyr Ile Leu Lys Thr Lys Asp Gly
                                       1050                                                          1080
GAA GAA GTA GAT ATA AAT AAT ATA TCT AAT TAT TGG ATA AGA AAA GAA AGA TTA ACA TCT
Glu Glu Val Asp Ile Asn Asn Ile Ser Asn Tyr Trp Ile Arg Lys Glu Arg Leu Thr Ser
                                       1110                                                          1140
ATA AGT GAT GAT TGG GAG TTA AGC AAC TTC AAA TTA ATA GCA AAT GGA AAA GTA ATA CAA
Ile Ser Asp Asp Trp Glu Leu Ser Asn Phe Lys Leu Ile Ala Asn Gly Lys Val Ile Gln
                                       1170
CAA CAA GAT GTA AAT AAA GTT TTT ACA GGT AAC GAA ACT TAT TAC ATA AAT AAA TAA
Gln Gln Asp Val Asn Lys Val Phe Thr Gly Asn Glu Thr Tyr Tyr Ile Asn Lys End
```

FIG._2.
PAGE 2 OF 2

CLONING AND EXPRESSION OF PHOSOPHOLIPASE C GENES

FIELD OF THE INVENTION

This invention relates generally to the application of recombinant DNA technology to understand and treat medical diseases and, more particularly, to the cloning, expression and modification of DNA sequences encoding bacterial proteins or fragments thereof.

BACKGROUND OF THE INVENTION

The anaerobic spore-forming bacilli of the genus Clostridium represent a major class of human pathogens, causing, inter alia, botulism, tetanus and gas gangrene. For the most part, the pathogenicity depends largely on the release of extremely toxic exotoxins or highly destructive enzymes.

One of the most lethal and necrotizing toxins produced by many of the Clostridium species associated with invasive infection in humans is a calcium-dependent enzyme lecithinase, known as Phospholipase C (EC3.1.4.3). This enzyme catalyzes the breakdown of lecithin (choline phosphoglyceride) in cell membranes to diglyceride and phosphorylcholine, as well as the hydrolysis of cephalin and sphingolmyelin. Primarily through its action on lecithin, which is present in membranes of many cells, the toxin can cause extensive damage in a variety of animal tissues. (See, generally, Mollby, R., "Bacterial Phospholipases," in *Bacterial Toxins and Cell Membranes*, Eds. Jeljaszewicz and Wadstrom (1977), which is incorporated herein by reference.)

Although much research has been conducted on the various activities of purified Clostridium Phospholipase C (see, e.g., Yamakama and Ohsaka, J. Biochem 81:115-126 (1977), which is incorporated herein by reference, little is known about its structure (e.g., amino acid sequence). This is in part due to the risks associated with the production of large quantities of substantially pure Phospholipase C, which can necessitate growing large volumes of typically toxic Clostridium bacteria. Commonly used processes for purification do not, of course, guarantee removal of other Clostridium toxins. Also, most assays for Phospholipase C are time consuming and difficult to perform with high degrees of accuracy and reproducibility.

In general, the species diagnosis of most Clostridium infections is complicated by the fact that many such infections contain more than one type of bacteria. This diagnosis could rely on the detection of particular species variants of Phospholipase C. In this regard, isolating genes encoding Clostridium Phospholipase C is desirable, particularly in view of the cloning and expression of Phospholipase genes from other virulent bacteria species (e.g., *P. aeruginosa*, Pritchard and Coleman, *J. Bacteriol.* 167:291-298 (1986) and *S. aureus*, Coleman et al., *Microb. Path.* 1:549-564 (1986), both of which are incorporated herein by reference.)

Thus, there exists a need for the safe and economic production of substantial quantities of Clostridium Phospholipase C, as well as new and improved assays for the toxin. Ideally, the material will be substantially free of other, naturally-occurring Clostridium proteins The present invention fulfills these needs.

SUMMARY OF THE INVENTION

The present invention provides cloned recombinant DNA sequences coding for Clostridium Phospholipase C polypeptides, which sequences when operably linked to an expression control sequence and expressed in a host produce Clostridium Phospholipase C, or fragments thereof, substantially free from naturally-associated Clostridium gene products. Novel polypeptides having a portion of the primary structure of Clostridium Phospholipase C and/or one or more of the biological properties of the toxin can be readily produced by modifying the DNA sequences encoding the naturally occurring genes. The genes also may be used as probes for isolating related genes and identifying the presence of Clostridium in samples from human patients. Further, the gene expression products can be used in various other diagnostic and therapeutic applications, including the production of specifically reactive immunoglobulins.

BRIEF DESCRIPTION OF THE FIGURES

FIG. 1 depicts the nucleotide sequence and putative corresponding amino acid sequence of a DNA segment encoding *Clostridium perfringens* Phospholipase C. The arrow after amino acid 22 indicates a possible processing site of the signal peptide.

FIG. 2 depicts the nucleotide sequence and putative corresponding amino acid sequence of a DNA segment encoding *Clostridium bifermentans* Phospholipase C. The arrow after amino acid 23 indicates a possible processing site of the signal peptide.

DETAILED DESCRIPTION OF THE INVENTION

In accordance with the present invention, DNA sequences encoding polypeptide sequences of Clostridium Phospholipase C (PLC) enzymes are provided. When placed in expression vectors and suitable eukaryotic and prokaryotic hosts, large quantities of polypeptides displaying one or more of the various biological properties of naturally-occurring Clostridium PLC can be produced. These polypeptides are useful in the diagnosis and treatment of Clostridium infections.

In one aspect, the present invention contemplates isolating recombinant DNA segments encoding Clostridium PLC polypeptides, the DNA segment comprising a DNA sequence selected from group consisting of: (a) the DNA sequence of Clostridium perfringens PLC as shown in FIG. 1 and the DNA sequence of Clostridium bifermentans shown in FIG. 2, or their complementary strands; (b) DNA sequences, or their complementary strands, which on expression code for the polypeptide sequences shown in FIGS. 1 and 2 due, e.g., due to codon degeneracy; and DNA sequences (e.g., from other Clostridium species) which hybridize, typically under stringent conditions, to the DNA sequences of (a) or (b) above and which produce a polypeptide exhibiting at least one biological activity of PLC. The hybridizing sequences, including those encoding native or mutated gene sequences, will usually be at least about 50 to 60% homologous, preferably 85 to 90% homologous or more, to similarly-sized portions of the gene sequences in the Figures.

The DNA segment will typically further include an expression control DNA sequence operably linked to the PLC coding sequences, including naturally-associated promoter regions. Preferably, the expression control sequences will be prokaryotic promoter systems in vectors capable of transforming or transfecting prokaryotic host cells. Once the vector has been incorporated into the appropriate host, the host is maintained under conditions suitable for high level expression of the nucleotide sequences, and, as desired, the collection and purification of the Clostridium PLC polypeptides may follow.

Two putative amino acid sequences based on isolated and purified nucleotide sequences of genes coding for polypeptides of the present invention are shown in FIGS. 1 and 2. The initial 22 amino acids in FIG. 1 and 23 amino acids in FIG. 2 are rich in hydrophobic amino acids, as would be expected for a leader or signal sequence of a secreted mature protein.

It is well known that native forms of this "mature" Clostridium PLC will vary among Clostridium species in terms of length by deletions, substitutions, insertions or additions of one or more amino acids in the sequences. Common species of Clostridia from which various pertinent DNA sequences can be obtained include *C. perfringens, C. bifermentans, C. tertium,* and *C. sporogenes, C. novyi, C. septicum,* and *C. histolyticum*. Samples of these species can be obtained from a variety of sources, such as the American Tissue culture Collection, ("Catalogue of Bacteria, Phages and rDNA vectors," Sixteenth edition (1985) Rockville, Maryland, U.S.A., which is incorporated herein by reference).

In addition to these naturally-occurring forms of Clostridium PLC, other Clostridium PLC peptides can be readily designed and manufactured utilizing various recombinant DNA techniques well known to those skilled in the art. For example, polypeptides can vary at the primary structure level by amino acid substitutions, terminal and intermediate additions and deletions, and the like. Alternatively, polypeptide fragments comprising only a portion of the primary structure may be produced, which fragments possess one or more Clostridium PLC activities (e.g., enzyme activity), while exhibiting lower immunogenicity). In particular, it is noted that like many genes, the Clostridium PLC genes may contain separate functional regions, each having one or more distinct biological activities. These may be fused to functional regions (e.g., specific binding regions) from other genes (e.g., immunoglobulins, see, EPO No. 84302368.0, which is incorporated herein by reference) to produce fusion proteins (e.g., immunotoxins) having novel properties. In general, modifications of the genes may be readily accomplished by a variety of well-known techniques, such as site-directed mutagenesis (see, Gillman and Smith, Gene 8:81–97 (1979), which is incorporated herein by reference) which can be employed to generate various analogs and derivatives of naturally-occurring, mature Clostridium PLC.

The activities of Clostridium PLC polypeptides of the present invention can be assayed by a number of well-known techniques. A preferred assay procedure was developed by Krug and Kent (*Methods Enzymol.* 72:347–351 (1981) *Arch. Biochem. Biophys.* 231:400–410 (1984), which are incorporated herein by reference). Also, PLC activity can be determined by the hydrolysis of p-nitrophenylphosphorylcholine (Berka et al, *J. Bacteriol.* 152:239–245 (1982), which is incorporated herein by reference).

In another assay, egg yolk is utilized in agar medium, and active enzyme activity is indicated by the discoloration of the agar medium. Recently, other more sophisticated methods have been developed, see, e.g., U.S. Pat. No. 4,140,579, which is incorporated herein by reference, and can be utilized to assay the activities of the polypeptides of present invention.

As stated previously, the DNA sequences encoding the polypeptides of the present invention will be expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors will contain selection markers, e.g., tetracycline or neomycin, to permit detection of those cells transformed with the PLC DNA sequences (see, e.g., U.S. Pat. No. 4,704,362, which is incorporated herein by reference).

*E. coli* is the preferred prokaryotic host for cloning and expressing the DNA sequence of the present invention. Other microbial hosts suitable for use include bacilli, such as *Bacillus subtilus,* and other enterobacteriaceae, such as Salmonella, Serratia, and various Pseudomonas species. In these prokaryotic hosts, the expression vectors will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast may also be used for expression. Saccharomyces is a preferred host, with suitable vectors having expression control sequences, such as promoters, including 3-phosphoglycerate kinase or other glycolytic enzymes, and an origin of replication, termination sequences and the like as desired.

In addition to microorganisms, mammalian tissue cell culture may also be used to produce the polypeptides of the present invention (see, Winnacker, "From Genes to Clones," VCH Publishers, N.Y., N.Y. (1987), which is incorporated herein by reference). A number of suitable host cell lines have been developed, and include the CHO cell lines, the various COS cell lines, HeLa cells, myeloma cell lines, etc. Expression vectors for these cells can include expression control sequences, such as an origin of replication, a promoter, and necessary processing information sites, such as ribosome binding sites, RNA splice sites, polyadenalation sites, and transcriptional terminator sequences. Preferred expression control sequences are promoters derived from SV40, from Adenovirus, Bovine Papilloma Virus, and the like.

The vectors containing the DNA segments of interest (e.g., the PLC encoding sequences and expression control sequences) can be transferred into the host cell by well-known methods, which vary depending on the type of cellular host. For example, calcium chloride transfection is commonly utilized for prokaryotic cells, whereas calcium phosphate treatment may be used for other cellular hosts. (See, generally, Maniatis et al. *Molecular Cloning: A Laboratory Manual,* Cold Spring Harbor Press, (1982), which is incorporated herein by reference.)

Once expressed, the polypeptides of the present invention can be purified according to standard procedures of the art, including ammonium sulfate precipitation, fraction column chromatography, gel electrophoresis and the like. Once purified, partially or to homogeneity as desired, the polypeptides may then be used in developing and performing assay procedures, such as an antigenic substance for eliciting specific immunoglobulins useful in immunoassays, immunofluorescent stainings, and the like. Either polyclonal antiserum or a more specific monoclonal antibody composition reactive with any of the various epitopes on the polypeptides may be produced in accordance with well-known procedures. (See, generally, *Immunological Methods*, Vols. I and II, Eds. Lefkovits and Pernis, Academic Press, New York, N.Y. (1979 and 1981).)

The naturally-occurring PLC Clostridium genes from various Clostridium species may be identified and isolated utilizing well-known hybridization technology. In view of differing homology among the various PLC genes, the stringency of hybridization conditions must be adjusted from species to species. Filter hybridization is preferred, the hybridization buffer and procedures of which are generally described in *Nucleic Acid Hybridization: A Practical Approach*, Eds. Hames and Haggins, IRL Press, Washington, D.C. (1985), which is incorporated herein by reference.

Hybridization conditions sufficiently stringent to prevent hybridization to irrelevant nucleic acid sequences are used either during the hybridization or any of the wash steps. The precise degree of stringency can be controlled by temperature, probe concentration, probe length, ionic strength, time, and the like. Most conveniently, stringency is varied through manipulation of a polar organic solvent, such as formamide, or by varying temperatures. Typically, formamide will be present at a concentration ranging from about 20% to 50%, typically the higher percentages. Temperatures will typically be in the range of about 37° C. to 75° C., preferably about 42° C. to 45° C. Incubation times can vary from a few hours, to 24 to 36 hours or more, as desired.

A common suitable hybridization solution employs about 50% formamide, with 0.5 to 1 M sodium chloride, about 0.05 to 0.1 M buffers, such as sodium citrate, Tris, HEPES or PIPES, about 0.05 to 0.2% detergent and a protein source such as serum albumin. Other additives, such as carrier nucleic acids, volume exclusion agents, and the like may be included as desired.

For nucleic acid based diagnostic purposes, in situ hybridizations are preferred (see, Singer et al., Biotechniques 4:230–250 (1986) and U.S. Pat. No. 4,358,535, both of which are incorporated herein by reference). Synthetically produced nucleic acid probes ranging from about 10 to 50, preferably 100 to 200 nucleotides or more, are utilized to detect the presence of desired nucleic acid sequences. Typically, these probes are radioactively labeled, either by nick translation when produced from larger nucleic acid sequences, or by a variety of other means well known in the art. The samples may be obtained from any of a variety of human fluids, such as urine, saliva, or blood suspected of harboring the infectious organism or its nucleic acids.

The following examples are offered by way of illustration, not by limitation.

EXPERIMENTAL

Example 1

CLONING OF *C. PERFRINGENS*

*C. perfringens* (ATCC 13124) bacterial cells were collected by centrifugation, resuspended in 25 mM Tris, pH 8.0, 10 mM EDTA, 50 mM glucose, 4 mg/ml lysozyme and incubated 10 min at 23° C. SDS was added to a final concentration of 0.2%, and proteinase K to a final concentration of 100 μg/ml, and the sample incubated at 37° C. for 4 hr. The sample was extracted with an equal volume of phenol 2 times, and then 2 volumes of ethanol were added to the aqueous phase without mixing. The DNA was spooled from this solution with a glass rod, incubated with 2 mg/ ml RNAse and extracted with phenol. It was then precipitated with ethanol, dried, and resuspended in TE buffer (10 mM Tris, pH 7.4, 1 nM EDTA). The chromosomal DNA was digested with either HindIII or EcoRI and cloned into the respective sites in the plasmid pEMBL8+ (Dente, et al, (1983), *Nucl. Acids Res.* 11, 1645–1655, which is incorporated herein by reference) as follows. About 5 μg purified Clostridium DNA was digested with HindIII. The sample was extracted with phenol, precipitated with ethanol, and resuspended in TE. About 2 μg pEMBL8+ DNA was digested with HindIII, then diluted 1:5 in TE buffer and 2.5 units calf intestinal phosphatase added and incubated for a further hr at 65° C. The sample was extracted with phenol, precipitated with ethanol and resuspended in TE. The HindIII-digested Clostridium and pEMBL8+ DNAs were then ligated together, using T4 DAN ligase (New England Biolabs), and the ligated DNA transformed into *E. coli* according to standard methods (Maniatis et al., Cold Spring Harbor Laboratory, Cold Spring Harbor NY, 1982, pp. 250–251). The same process was performed with EcoRl.

The HindIII and EcoRI generated plasmids were then used to transform *E. coli* host DHI (Hanahan (1983), *J. Mol. Biol.* 166, 557–580) and transformants were plated on LB agar plates containing 50 μg/ml ampicillin and 1% (V/V) sheep red blood cells. After screening 2,000 transformants from each library, a total of five colonies that created zones of hemolysis were isolated.

All five isolates exhibit phospholipase C activity in their periplasmic space as assayed by the method of Krug and Kent (supra). Restriction analysis of the two kinds of plasmid (HindIII and EcoRI generated recombinants) in these colonies indicated they shared a common 2.0 kilobase (kb) EcoRl-HindIII fragment in their inserts. This 2.0 kb EcoRl-HindIII fragment was then subcloned between the EcoRI and HindIII site of pEMBL8+ for detailed restriction and DNA sequence analysis. *E. coli* transformants harboring the resulting plasmid, p8PLC, are hemolytic and exhibit phospholipase C activity in the periplasmic space, confirming that the gene is intact in this 2.0 kb fragment. Furthermore, a predominant protein with molecular weight of 43,000 KD is present in the osmotic shock fluid (Nossal and Heppel (1966) *J. Biol. Chem.* 241, 3055–2062) from the periplasmic space of DHl/p8PLC. This protein is absent from the shock fluid of the host cell.

Table I shows the PLC enzymatic activity obtained from PLC polypeptides (non-glycosylated) of the present invention in comparison to naturally-occurring Clostridium PLC. The recombinantly produced polypeptides were obtained from the periplasmic space of the transformed organisms by osmotic shock. A cell pellet was obtained from about 250 ml of the cultures, and the cells washed in 50 mM Tris-HCl, ph7.8, and centrifuged. The pellet was resuspended in 20 ml of the wash buffer containing 40% sucrose, to which was added EDTA to 2 mM. After 10 minutes, the solution was centrifuged and the cell pellets resuspended in 10 ml of cold H$_2$O, which was left standing on ice for about 10 minutes. This solution was centrifuged and the supernatant contained the shock fluid.

The assay, a PLC-alkaline phosphatase coupled assay, was performed as follows.

Reagents

| | |
|---|---|
| Tris-HCl, | 0.4 M, pH 7.3 at 37° |
| Calcium chloride, | 50 mM |
| Bovine serum albumin, | 1 mg/ml |
| Phosphatidylcholine, | 10 mM in absolute ethanol |
| Ammonium sulfate, | 0.2 M |
| Alkaline phosphatase (E. coli, Sigma Chemical Co., type III-S), | 100 u/0.3 ml of 2.5 M (NH$_4$)$_2$SO$_4$ suspension |
| Sodium dodecyl sulfate, | 20% |
| Ascorbate-molybdate reagent: | 1 part 10% ascorbic acid and 6 parts 0.42% ammonium molybdate in 1 N H$_2$SO$_4$ |

Procedures

Reagents are added in the following order and to the final concentrations indicated (final volume =40 μl): 50 mM Tris-HCl, 6.3 mM calcium chloride, 0.13 mg/ml bovine serum albumin. 2.5 mM phosphatidylcholine, 70 mM ammonium sulfate (including the amount of ammonium sulfate contributed by the suspension of alkaline phosphatase), 0.15 unit of alkaline phosphatase, and 0.1 to 1×10$^{-3}$ unit of phospholipase C. Routinely, all the assay components except phospholipase C may be combined as one large suspension, and aliquots can be removed for each assay. The assay mixture is incubated at 37° for 15 min in a shaking water bath. The reaction is terminated by addition of 40 μl of sodium dodecyl sulfate, then 200 μl of ascorbic-molybdate reagent is added, followed by incubation at 45° for 20 min or 37° for 60 min. The absorbance is determined at 820 nm. One nanomole of inorganic phosphate corresponds to a net absorbance of about 0.045 above a reaction mixture blank absorbance of 0.040. One unit of phospholipase C activity is defined as that which produces 1 μmol of inorganic phosphate per minute.

TABLE I

| Assay for Phospholipase C (PLC) | | | |
|---|---|---|---|
| | PLC assay A$_{820}$ reading (vol/dilution) | Protein concentration (mg/ml) | Specific activity (units/mg) |
| Osmotic shock fluid from E. coli transfected with p8PLC | .542 (20 μl/1:100) | 0.56 | 107 |
| Purified PLC from E. coli transfected with p8PLC | .520 (20 μl/1:100) | 0.76 | 79 |
| Purified PLC from Clostridium perfringens | .440 (20 μl/1:100) | 0.29 | 184 |

Sequence analysis (Sanger et al, (1977) Proc. Natl. Acad. Sci. 74, 5463–5467) of the 2.0 kb EcoRI-HindIII fragment revealed an open-reading frame of 1196 base pairs (bp) located in the HindIII half of the fragment (FIG. 1). The sequence codes for a 22 amino acid putative signal peptide and a 377 amino acid mature protein, the amino acid composition of which agrees well with that of prior reports (Krug and Kent, supra).

Example 2

CLONING OF PHOSPHOLIPASE C GENE FROM C BIFERMENTANS

C. bifermentans (ATCC 638) cells were prepared and DNA extracted as in Example 1. Then, the chromosomal DNA was digested with EcoRI and cloned into the EcoRI site of λgt10 arms (Stratagene, Inc.) and packaged (Huynh et al, (1984) DNA Cloning Techniques; A practical Approach, David Glover, ed. IRL Press, Oxford 50–70, which is incorporated herein by reference). The genomic library was plated on *E. coli* host C600 Hfl and screened by plaque hybridization (Benton and Davis (1977) *Science* 196, 180–182) using the previously cloned *C. perfringens* phospholipase C gene as a probe. Hybridization was performed at 5 x SSC/50% formamide/1X Denhardt/0.2% SDS/0.1 mg/ml calf thymus DNA at 30° C. overnight. After screening 2,000 plaques, a total of 20 plaques that hybridized to the probe were isolated. All of these plaques contain a 2.5 kb EcoRI insert that was later subcloned into pEMBL8+ to form plasmid pCBPLCl. Restriction and Southern analysis was performed by digesting with EcoRI and HindIII, running the fragments on agarose gel and transferring the dispersed fragments to nitrocellulose (Southern (1975) *J. Mol. Biol.* 98, 503–518). DNA on the nitrocellulose was hybridized to a radioactive probe prepared from the previously cloned *C. perfringens* gene by nick translation (Maniatis et al., supra at pgs. 387–389 and 109–112). Only the 0.83 kb HindIII - EcoRl fragment hybridized. This indicated that the sequence related to the *C. perfringens* phospholipase C gene is located only in that fragment at the end of the insert. DNA sequence analysis of this fragment confirmed that it indeed contains part of the phospholipase C coding sequence, but is truncated at the EcoRI site. So a second genomic library was created to isolate the missing coding sequence.

The second library was created by cloning HindIII-digested chromosomal DNA from *C. bifermentans* into the HindIII site of pUC19 (Norrander et al, (1983) Gene 26, 101–110, which is incorporated herein by reference). *E. Coli* transformants containing the recombinant plasmids were then screened by colony hybridization (Norrander, J., et al, supra) using the 0.83 kb HindIII - EcoRl fragment from pCBPLCI as a probe. From 2,000 transformants, seven colonies that hybridized to the probe were isolated. All plasmids in these colonies, of which a representative one is called pCBPLC2, contain a 5.2 kb HindIII fragment in their inserts. The 1.0 kb EcoRl fragment that is adjacent to the EcoRI insert of pCBP in the chromosome was subcloned from pCBPLC2 into pCBPLCl to reconstitute the entire phospholipase C gene. The resulting plasmid is called pCBPLC3. The entire coding sequence for phospholipase C in pCBPLC3 is shown in FIG. 2. The gene codes for a protein of 377 amino acid residues, with approximately 20 N-terminal residues corresponding to a signal peptide.

The *C. Perfringens* and *C. Bifermentans* phospholipase C proteins have an overall amino acid homology of 51%. The two genes have overall homology at the nucleotide level of 64%.

Example III

DNA of the plasmid p8PLC, containing the complete *Clostridium perfringens* PLC gene, was cut at the unique AccI site, which occurs at nucleotides 76–81 of the PLC sequence (FIG. 1). The ends were filled in using the Klenow fragment of polymerase 1. Xba linkers (New England Biolabs) were treated with polynucleotide kinase and then ligated to the cut plasmid DNA, using T4 DNA ligase. The ligated DNA was cut with XbaI, and then run on a 1% agarose gel. The linear plasmid DNA was purified from the agarose, ligated again, and transformed into E. coli.

A colony was picked, plasmid DNA purified (denoted p8PLC-Xba), and sequenced around the XbaI linker insert. The construction had the effect of deleting amino acid 26, Val, and inserting at the deletion four amino acids: Gly Ser Arg and Ala. The mutant protein was purified and assayed. There was no detectable difference in its activity relative to normal PLC.

Example IV

DNA of the plasmid p8PLC was cut with EcoRl, which cuts about 800 nucleotides upstream of the pLC gene. The cut plasmid was treated with the nuclease Bal31, which progressively removes nucleotides from the free DNA ends produced by the cut. The DNA was filled in with the Klenow fragment, ligated with XbaI linkers and cut with XbaI as well as HindIII, which cuts at the end of the PLC gene. The DNA was run on an agarose gel, and XbaI - HindIII fragments were isolated, of a size corresponding to removal of 0–100 nucleotides from the beginning of the PLC gene. These fragments were ligated with the large XbaI - HindIII fragment of p8PLC-Xba and transformed into E. coli. DNA was extracted from various colonies and sequenced around the XbaI site.

Two such mutants were selected for further study. In one mutant, RICHyb-3, the mutated PLC gene in p8PLC-Xba had been further changed by deletion of amino acids 27–30, Tyr Ala Trp Asp. In the other mutant RICHyb-9, amino acids 27–35, Tyr...Gly, had been deleted. The hemolytic activity of the mutant PLC proteins were respectively reduced approximately 10-fold and 50-fold relative to the normal PLC protein.

From the foregoing, it will be appreciated that the DNA sequences of the present invention provide improved means for the safe and economic production of substantial quantities of Clostridium Phospholipase C. polypeptides. Importantly,, the Clostridium Phospholipase C products are produced substantially free from other, naturally-occurring Clostridium proteins. The invention also provides to those skilled in the art means for improved assay procedures for the detection of Clostridium species in samples, either through immunologic or DNA hybridization techniques.

Although the invention has been described in some detail by way of illustration and example for purposes of clarity of understanding, it will be apparent that certain changes and modifications may be practiced within the scope of the appended claims.

We claim:

1. An isolated recombinant DNA segment encoding a Clostridium Phospholipase C polypeptide, said DNA segment comprising a first DNA sequence selected from the group consisting of:
  (a) the DNA sequences of FIGS. 1 and 2, or their complementary strands;
  (b) DNA sequences which on expression code for the polypeptide sequences of FIGS. 1 and 2, or the complementary strands of said DNA sequences; and
  (c) DNA sequences which hybridize under stringent conditions to sequences of (a) or (b).

2. A DNA segment of claim 1, further comprising an expression control DNA sequence operably linked to said first DNA sequence.

3. A DNA segment of claim 2, wherein the expression control sequence comprises a prokaryotic promoter system.

4. A DNA segment of claim 2, wherein the expression control DNA sequence is selected from the group consisting of a lac promoter, a trp promoter, and a major operator and promoter region of phage lambda.

5. A DNA segment of claim 1, further comprising a bacterial cloning vector.

6. A DNA segment of claim 1, further comprising a signal sequence operably linked to said first DNA sequence.

7. A prokaryotic or eukaryotic host cell transformed or transfected with a DNA segment according to claim 1, 2, or 5.

8. A recombinant vector which, in a transformed or transfected host, will express a DNA segment coding for a Clostridium Phospholipase C polypeptide.

9. A prokaryotic or eukaryotic host cell transformed or transfected with a recombinant vector according to claim 8.

10. A process for producing a Clostridium Phospholipase C polypeptide comprising the steps of:
  (a) forming a vector comprising a nucleotide sequence coding for said polypeptide, said sequence operably linked to an expression control sequence;
  (b) transforming or transfecting a host cell with the vector; and
  (c) maintaining the host cell under conditions suitable for expression of the nucleotide sequence.

11. A process according to claim 10, wherein the nucleotide sequence is the DNA sequence of FIG. 1 or FIG. 2.

12. A process according to claim 10, wherein the host is a microorganism.

13. A process according to claim 12, wherein the microorganism is E. coli.

14. A process according to claim 10, further comprising purifying the expressed polypeptide.

15. A process according to claim 10, wherein the expressed polypeptide is non-glycosylated.

16. A process according to claim 10, wherein the polypeptide has a naturally associated leader sequence.

17. A cloned gene coding for a Clostridium Phospholipase C, wherein said gene is substantially free from naturally associated Clostridium genes.

18. A cloned gene according to claim 17, wherein the gene is isolated from Clostridium perfringens or Clostridium bifermentans.

* * * * *